United States Patent [19]

Kubo et al.

[11] Patent Number: 4,894,457
[45] Date of Patent: Jan. 16, 1990

[54] 7-BROMO-BETA-CARBOLINE COMPOUND AND METHOD FOR PRODUCING SAME

[75] Inventors: Masaaki Kubo, Sayama; Hiroshi Umezawa; Kazuhiro Okura, both of Kawagoe, all of Japan

[73] Assignee: Kawaken Fine Chemicals Co., Ltd., Tokyo, Japan

[21] Appl. No.: 135,392

[22] Filed: Dec. 21, 1987

[30] Foreign Application Priority Data

Dec. 25, 1986 [JP] Japan .................................. 61-310496

[51] Int. Cl.$^4$ ............................................. C07D 471/04
[52] U.S. Cl. ......................................... 546/85; 546/86; 546/87
[58] Field of Search .............................. 546/85, 86, 87

[56] References Cited

FOREIGN PATENT DOCUMENTS 0011059  5/1980  European Pat. Off. .............. 546/51
0021857  1/1981  European Pat. Off. .............. 546/85

OTHER PUBLICATIONS

Journal of the American Chemical Society, vol. 109, No. 11, 1987, Kenneth L. Rinehart: "Eudistomins A Q, Beta-Carbolines from the Antiviral Caribbean Tunicate Eudistoma Olivaceum", pp. 3378–3387; p. 3384, line 59, p. 3380, Scheme II.

*Primary Examiner*—Alan L. Rotman
*Attorney, Agent, or Firm*—McAulay Fisher Nissen & Goldberg

[57] ABSTRACT

A 7-bromo-β-carboline compound of the formula (I):

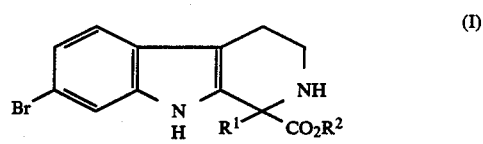

(I)

wherein $R^1$=H or $C_1$–$C_5$ alkyl and $R^2$=$C_1$–$C_5$ alkyl or benzyl, is produced by reacting a β-carboline compound of the formula (II):

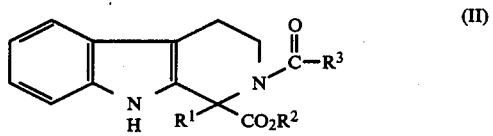

(II)

wherein $R^1$ and $R^2$ are as defined above and $R^3$=H, $C_1$–$C_5$ alkyl, $C_1$–$C_5$ alkoxy or benzyloxy, with a brominating agent in an organic solvent in the presence of an alkalic and then hydrolyzing the resultant procursory 7-bromo-β-carboline compound of the formula (III):

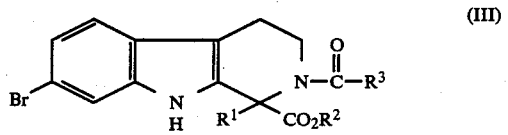

(III)

is a solvent in the presence of a mineral acid.

9 Claims, No Drawings

7-BROMO-BETA-CARBOLINE COMPOUND AND METHOD FOR PRODUCING SAME

BACKGROUND OF THE INVENTION

1. Field of the Invention

The present invention relates to a 7-bromo-β-carboline compound and a method for producing the same. More particularly, the present invention relates to a 7-bromo-β-carboline compound which is usable as an intermediate of alkaloid compounds, for example, indol alkaloid compounds having a 6-bromoindol structure, and useful as medicines and pesticides.

2. Description of the Related Art

The 7-bromo-β-carboline compounds of the present invention are novel, and thus the method of the present invention for producing the same is also novel and cannot be known from the prior art.

In view of the chemical structure of the 7-bromo-β-carboline compound, it is assumed that the compound could be produced by, for example, condensing a 6-bromotryptamine compound with an α-ketoacid ester. However, the preparation of the 6-bromotryptamine compound is very difficult and cannot be produced by a mere conventional bromination of the corresponding tryptamine compound. When a β-carboline compound in which the amino group in a 2-position is not protected by a protecting substituent, is brominated, mainly, a bromine atom is introduced into the 6-position to produce a 6-bromo-β-carboline, but not into a 7-position.

Accordingly, the 7-bromo-β-carboline compound of the present invention was not known before the present invention and is produced for the first time by the method of the present invention.

SUMMARY OF THE INVENTION

An object of the present invention is to provide a novel 7-bromo-β-carboline compound and a method for producing the same at a high yield and at a high selectivity.

The 7-bromo-β-carboline compound of the present invention has the formula (I):

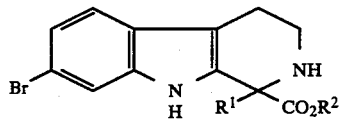

(I)

wherein $R^1$ represents a member selected from the group consisting of a hydrogen atom and alkyl radicals having 1 to 5 carbon atoms, for example methyl, ethyl, propyl, butyl and pentyl radicals, and $R^2$ represents a member selected from the group consisting of alkyl radicals having 1 to 5 carbon atoms, for example, methyl, ethyl, propyl, butyl, and pentyl radicals and a benzyl radical.

The 7-bromo-β-carboline compound of the formula (I) is produced by the method of the present invention which comprises the steps of:

(A) reacting a β-carboline compound of the formula (II):

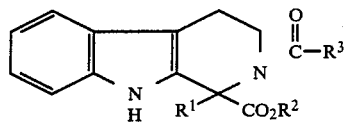

(II)

wherein $R^1$ and $R^2$ are as defined above, and $R^3$ represents a member selected from the group consisting of a hydrogen atom, alkyl radicals having 1 to 5 carbon atoms, for example, methyl, ethyl, propyl, butyl and pentyl radicals, alkoxy radicals having 1 to 5 carbon atoms, for example, methoxy, ethoxy, and t-butoxy radicals and a benzyloxy radical, with a brominating agent in an organic solvent comprising at least one member selected from the group consisting of chlorine-containing organic liquid compounds and polar organic compounds in the presence of an alkali, to prepare a precursory 7-bromo-β-carboline compound of the formula (II):

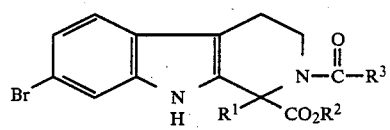

(III)

wherein $R^1$, $R^2$, and $R^3$ are as defined above; and (B) hydrolyzing the precursory compound of the formula (III), in a solvent in the presence of a mineral acid.

DESCRIPTION OF THE PREFERRED EMBODIMENTS

The 7-bromo-β-carboline compound of the formula (I) of the present invention is preferably selected from the group consisting of, for example, 7-bromo-1-methyl-1-methoxycarbonyl-1,2,3,4-tetrahydro-β-carboline, 7-bromo-1-methyl-1-ethoxycarbonyl-1,2,3,4-tetrahydro-β-carboline, 7-bromo-1-ethoxycarbonyl-1,2,3,4-tetrahydro-β-carboline and 7-bromo-1-benzyloxycarbonyl-1,2,3,4-tetrahydro-β-carboline. The above-mentioned compounds are novel and are usuable as a precursor of various indol alkaloids having a substituent in a 7-position thereof.

For example, 7-bromo-1-methyl-1-methoxycarbonyl-1,2,3,4-tetrahydro-β-carboline can be converted to a β-carboline alkaloid, which is useful as an amine oxidase inhibiter by the decarboxylation thereof under an acid condition to provide a corresponding 11-bromo-tetrahydroharmane and then substituting the 11-bromine atom in the 11-bromotetrahydroharmane by a methoxy or hydroxy radical in accordance with the following route.

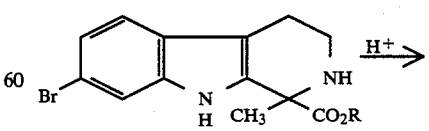

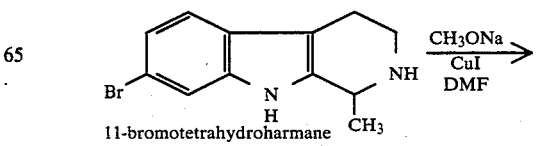

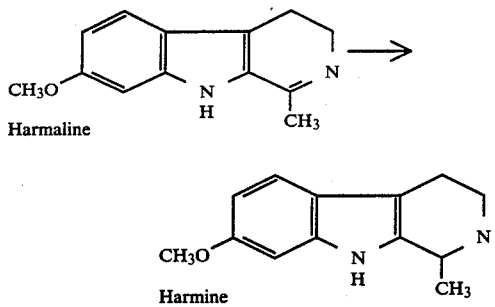

Also, the β-carboline compounds can be condensed with 5-halo-2-ethyl pentanal to produce an aspidosperma type alkaloid compound in accordance with the following routes.

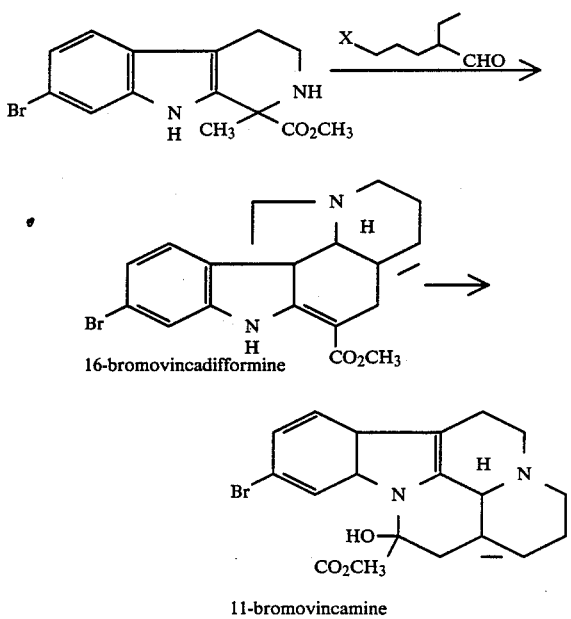

Especially, 16-bromovincadifformine can be converted to 11-bromovincamine, which is useful as a medicine having a cerebrovascular dilation effect, by the above-mentioned conversion method.

The starting β-carboline compound of the formula (II) for the method of the present invention can be easily produced by condensing, for example, tryptamme, with an α-keto-acid ester to provide 1-alkyl (or hydrogen)-1-alkoxy-carbonyl-1,2,3,4-tetrahydro-β-carboline and then, introducing a protective radical into the amino radical in the 2-position of the resultant carboline compound in a usual manner. The protective radical is preferably selected from formyl, acetyl, propionyl, k ethoxycarbonyl, benzyloxycarbonyl and tert-butyloxycarbonyl radicals.

The starting β-carboline compound of the formula (II) usable for the method of the present invention is preferably selected from the group consisting of 2-formyl, 2-acetyl, 2-benzyloxycarbonyl and 2-tert-butyloxycarbonyl derivatives of 1-methoxycarbonyl-1,2,3,4-tetrahydro-β-carboline, 1-methyl-1-methoxycarbonyl-1,2,3,4-tetrahydro-β-carboline, and 1-methyl-1-ethoxycarbonyl-1,2,3,4-tetrahydro-β-carboline, and 1-ethyl-1-methoxycarbonyl-1,2,3,4-tetrahydro-β-carboline.

The β-carboline compound of the formula (II) is reacted with a brominating agent in an organic solvent preferably comprising at least one member selected from the group consisting of chlorine-containing organic liquid compounds, for example, chloroform, dichloromethane, tetrachloromethane, and dichloroethane, and polar organic liquid compounds, for example, dimethylformamide and dimethylsulfoxide, in the presence of an alkali to provide a precursory 7-bromo-β-carboline compound of the formula (III).

The brominating agent preferably comprises at least one member selected from bromine and N-bromosuccineimide.

Usually, the brominating agent is used in an amount of 0.8 to 1.5 molar equivalent weight, preferably 0.9 to 1.2 molar equivalent weight per molar equivalent weight of the starting β-carboline compound of the formula (II).

The organic solvent usable for the reaction of the β-carboline compound is not limited to a specific type of solvent unless the organic solvent is inert to the reaction. Preferably, the organic solvent comprises at least one chlorine-containing organic liquid compound such as halogenated aliphatic hydrocarbon compound, for example, dichloromethane, chloroform or dichloroethane.

In the bromination reaction of the β-carboline compound of the formula (II), the presence of the alkali is effective for catching and neutralizing the reaction by-product, i.e., hydrogen bromide. The alkaki usable for the present invention is not limited to a specific alkaline compound, and preferably comprises at least one member selected from alkali carbonates, for example, sodium hydrogen carbonate, potassium hydrogen carbonate, and sodium carbonate; alkali disulfates, for example, sodium hydrogen sulfate; and alkali metal salts of organic acids, for example, formic acid, acetic acid, propionic acid, and benzoic acid.

Usually, the alkali is used in an amount of 0.5 to 1.5 molar equivalent weight, preferably 0.9 to 1.5 molar equivalent weight, per molar equivalent weight of bromine.

When alkali is not used, the reaction by-product, hydrogen bromide, causes a decomposition of the protective radical introduced to the 2-amino radical and the degree of position-selecting of the bromination reaction is thus significantly decreased.

The bromination reaction temperature is not specifically limited. However, the bromination reaction is exothermic and, therefore, is preferably carried out at a temperature lower than the boiling point of the organic solvent, for example, −30° C. to 50° C. Also, preferably the bromination reaction is carried out while the reaction mixture is cooled with water or ice water.

The bromination product, i.e., the precursory 7-bromo-β-carboline compound of the formula (III), is hydrolyzed with a mineral acid in anorganic solvent to remove the protective radical on the 2-amino radical and to provide the desired 7-bromo-β-carboline compound of the formula (I).

The protective radical-removing reaction is preferably carried out in a reaction medium comprising at least one organic liquid compound selected from alcohol compounds, for example, methyl alcohol, ethyl alcohol and propyl alcohol, and organic liquid acids, for example, acetic acid and propionic acid, and at least one mineral acid, for example, hydrogen chloride or hydrogen bromide dissolved in the organic solvent.

The mineral acid is usually used in an amount of 1.0 to 3.0 molar equivlent weight per molar equivalent weight of the precursory 7-bromo-β-carboline compound of the formula (III), to allow the resultant 7-bromo-β-carboline compound to be converted to a salt thereof.

The protective radical-removing reaction can be carried out at room temperaure or more, but at a temperature not exceeding the boiling point of the organic solvent. If the reaction temperature is excessively high, an undesirable decarboxylation reaction occurs on the resultant 7-bromo-β-carboline compound, and thus, preferably, the reaction temperature is 80° C. or less.

The resultant 7-bromo-β-carboline compound of the formula (I), which is free from the protective radical, can be directly isolated as a mineral acid salt thereof from the reaction mixture.

Usually, the protective radical-removing reaction product contains a small amount of 6-bromo derivative in addition to the desired 7-bromo derivative. The molar ratio of the 7-bromo derivative to the 6-bromo derivative is in the range of from 12:1 to 4:1. The resultant isolation product can be refined by neutralizing with an alkaline solution and then recrystallizing in a solvent. The refined product is substantially free from the 6-bromo derivative and has a high degree of purity.

The present invention will be further illustrated by way of specific examples, which are merely representative and do not restrict the scope of the present invention in any way.

EXAMPLE 1

Preparation of 7-bromo-1-methyl-1-methoxycarbonyl-1,2,3,4-tetrahydro-β-carboline A flask having a capacity of 1 liter was charged with a mixture consisting of 54.4 g of 2-formyl-1-methyl-1-methoxycarbonyl-1,2,3,4-tetrahydro-β-carboline, 560 ml of chloroform, and 20.2 g of sodium hydrogen carbonate, and the resultant dispersion mixture was stirred. The temperature of the dispersion mixture was controlled to a level of 0° C. to 5° C., 200 ml of a chloroform solution containing 32.0 g of bromine were gradually added dropwise to the reaction mixture over a period of 6 hours, and the resultant reaction mixture was aged for 2 hours at the above-mentioned temperature. Thereafter, 200 ml of water was mixed in the reaction mixture and the resultant admixture was stirred for 15 minutes. A chloroform phase was then separated from the admixture, and the separated chloroform fraction was subjected to distillation under a reduced pressure to remove chloroform. Accordingly, 69.5 g of a crude brominated 2-formyl-1-methyl-1-methoxycarbonyl-1,2,3,4-tetrahyro-β-carboline was obtained. When the crude product was subjected to gas chromatographic analysis, it was found that the crude product was a mixture of a 7-bromo isomer and 6-bromo isomer in a molar ratio of 4:1.

The crude product was dispersed in 50.0 g of methyl alcohol, 7.5 g chlorine gas was blown into the dispersion, and the resultant mixture was stirred at a temperature of 50° C. for 70 hours. Thereafter, the dispersion was cooled with ice water. The resultant deposited crystals were collected by filtration. The resultant product consisted of 30.4 g of white 7-bromo-1-methyl-1-methoxy-carbonyl-1,2,3,4-tetrahydro-β-carboline-hydrochloric acid salt powder in a yield of 59.4%. As a result of gas chromatographic analysis, it was confirmed that the resultant white powder contained no 6-bromo isomer.

The filtrate obtained by the above-mentioned filtration was mixed with 50 ml of water and then 40 ml of a 10% sodium carbonate aqueous solution were added dropwise to the mixture. The resultant admixture was distilled under a reduced pressure, to remove methyl alcohol from the admixture, and the resultant deposited crytals were collected by filtration. The crystals were recrystallized in methyl alcohol, and 7-bromo-1-methyl-1-methoxycarbonyl-1,2,3,4-tetrahydro-β-carboline in the form of a prism crystal was obtained in an amount of 3.94 g and at a yield of 10.7%.

The above-mentioned hydrochloric acid salt could be substantially quantitatively converted to a corresponding free compound by the above-mentioned method.

The free compound exhibited the following properties.

Melting point: 179° C. to 179.5° C.

MS m/z: 324 (M+, 3%), 322 (3%), 266 (12%), 365 (91%), 264 (15%), 263 (100%).

NMR (CDCl$_3$) δ: 1.67 (s, 3H, CH$_3$), 2.33 (s, 1H, NH), 2.70 (t, 2H, J=5, CH$_2$), 3.17 (t, 2H, J;32 5, CH$_2$), 3.75 (s, 3H, CO$_2$CH$_3$), 7.0~7.5 (m, 3H, aromatic-H), 8.3 (bs, 1H, indole-NH) ppm.

IR ν: 1740 (c=0) cm$^{-1}$

EXAMPLE 2

A solution was prepared by dissolving 2.86 g (10 m moles) of 1-methyl-1-methoxycarbonyl-2-formyl-1,2,3,4-tetrahydro-β-carboline and 1.01 g of sodium hydrogen carbonate in 140 ml of chloroform, and a solution of 1.6 g (10 m moles) of bromine in 20 ml of chloroform was added dropwise to the above-mentioned β-carboline compound solution over a period of one hour while cooling with ice water and stirring the solution. The temperature of the resultant reaction mixture was maintained at a level of from 0° c. to 5° C.

The reaction mixture was stirred at the above-mentioned temperature for 2 hours and then admixed with 100 ml of water. A chloroform phase was separated from the admixture, was washed with water, and was distilled under a reduced pressure to remove chloroform therefrom.

A crude reaction product in the form of a light yellow powder was obtained in an amount of 4.02 g and at a yield of 110%.

As a result of gas chromatographic analysis, it was found that the crude reaction product consisted of a mixture of a 7-bromo isomer and a 6-bromo isomer in a molar ratio of 29:1.

The crude product was treated in the same manner as described in Example 1, to provide purified 7-bromo-1-methyl-1-methoxycarbonyl-1,2,3,4-tetrahydro-β-carboline.

EXAMPLES 3 to 6

In each of Examples 3 to 6, the same procedures as those described in Example 2 were carried out except that the solvent and alkali consisted of the compounds shown in Table 1, respectively.

The resultant crude reaction product contained 7-bromo isomer and 6-bromo isomer in amounts shown in Table 1.

TABLE 1

| Example No. | Bromination reaction Solvent | Bromination reaction Alkali | Crude reaction product 6-bromo isomer | Crude reaction product 7-bromo isomer |
| --- | --- | --- | --- | --- |
| 3 | CHCl$_3$ | NaOCOCH$_3$ | 14.4% | 85.6% |
| 4 | CHCl$_3$ | NaHCO$_3$ | 14.3% | 80.1% |
| 5 | CH$_2$Cl$_2$ | NaOCOCH$_3$ | 19.7% | 76.7% |
| 6 | CHCl$_3$ | NaOCOH | 15.5% | 78.8% |

EXAMPLE 7

2-benzyloxycarbonyl-1-methyl-1-methoxycarbonyl-1,2,3,4-tetra-hydro-β-carboline in an amount of 10.0 g (26 m moles) was dissolved in 100 ml of chloroform. The resultant solution was mixed with 2.2 g (26 m moles) of sodium acetate while being stirred. A solution of 4.2 g (26 m moles) of bromine in 50 ml of chloroform was added dropwise to the above-mentioned solution over a period of 6 hours while controlling the temperature of the resultant reaction mixture to a level of 0° C. to 5° C. and stirring the reaction mixture. Thereafter, the reaction mixture was further stirred for 2 hours at the above-mentioned temperature.

The reaction mixture was washed with a sodium carbonate aqueous solution, and then with water to neutralize same. The reaction mixture was then distilled under a reduced pressure to remove chaloroform, and 12.1 g of a crude brominated 2-benzyloxycarbonyl-1-methyl-1-methoxycarbonyl-1,2,3,4-tetrahydro-β-carboline in the form of a yellowish brown viscous oily liquid was obtained.

This oily liquid was dissolved in 100 ml of acetic acid and mixed with 50 ml of a 47% hydrobromic acid aqueous solution. The resultant mixture was stirred at a temperature of 30° C. to 34° C. for 18 hours. The mixture was then admixed with 200 ml lof cold water and 50 ml of toluene and the resultant admixture stirred for one hour. The admixture was allowed to be separated to a toluene phase and a water phase, and the toluene phase was removed from the admixture and the remaining water phase was mixed with ammonia water. The resultant alkaline aqueous solution was subjected to extraction with 100 ml of chloroform, and the extract was then distilled under a reduced pressure to remove chloroform therefrom. A light yellow solid substance was obtained, and the solid substance was recrystallized in methyl alcohol. The recrystallization comprised prism crystals of 7-bromo-1-methyl-1-methoxycarbonyl-1,2,3,4-tetrahydro-β-carboline in an amount of 7.50 g and at a yield of 88%. This product did not contain 6-bromo isomer.

EXAMPLE 8

Preparation of 7-bromo-1-methyl-1-ethoxycarbonyl-1,2,3,4-tetrahydro-β-carboline 1-methyl-1-ethoxycarbonyl-2-formyl-1,2,3,4-tetrahydro-β-carboline in an amount of 57.3 g (0.2 mole) was dissolved in 570 ml of chloroform and then 20.2 g (0.24 mole) of sodium hydrogen carbonate were added to the resultant solution. The resultant solution was stirred and cooled with ice water.

A chloroform solution of 16.0 g (0.2 mole) of bromine in an amount of 50 ml was added dropwise to the solution at a temperature of 0° C. to 5' C. over a period of 6 hours. The resultant reaction mixture was further paged for 2 hours, and was then mixed with 200 ml of water. The resultant chloroform phase was separated from the mixture and washed with 200 ml of water, and the washed chloroform phase was distilled under a reduced pressure to remove chloroform.

A light brown solid substance was obtained, and a solution of 7.4% by weight of hydrogen chloride in ethyl alcohol was mixed with the light brown solid substance. The resultant mixture was stirred at a temperature of 50° C. for 40 hours and then cooled with ice water. The resultant deposited white solid particles were collected by filtration and were dried, and 40.8 g of a white powder was obtained. The filtrate was distilled under a reduced presure to remove about ⅔ of ethyl alcohol contained in the filtrate. The residual filtrate was cooled with ice to allow a white solid substance to deposit. An amount of 16.8 g of the white solid substance was collected and added to 40.8 g of the white powder.

The total of 7-bromo-1-methyl-1-ethoxycarbonyl-1,2,3,4-tetrahydro-β-carboline was obtained at a yield of 70% and had a melting point of 218.5° C., at which the compound was melt-decomposed.

NMR (CDCl$_3$) δ: 1,33 (t, 3LH, J=7, CH$_2$H$_3$), 1.67 (S, 3H, CH$_3$), 2.33 (S, 1H, NH), 2.70 (t, 2H, J=5, CH$_2$) 3.17 (t, 2H, J=5, CH$_2$), 4.38 (q, 2H, J=7, CO$_2$CH$_2$), 7.0∼7.5 (m, 3H, aromatic-H), 8.3 (bs, 1H, indol-NH) ppm

EXAMPLE 9

A four-necked flask having a capacity of 500 ml was charged with 68.1 g of 1-methyl-1-methoxycarbonyl-2-formyl-β-carboline, 25.2 g of sodium hydrogen carbonate, and 215 ml of N,N-dimethylformamide, and the mixture was stirred in the flask at a temperature of 0° to 5° C. A solution of 44.0 g of bromine in 143 ml of N,N-dimethylamide was then added dropwise to the mixture. After the dropwise addition was completed, the resultant reaction mixture was further stirred for one hour. Then, chloroform and water were added to the reaction mixture to effect an abstraction and separation of a chloroform fraction.

The chloroform fraction was washed with water and was distilled under a reduced pressure to remove chloroform. Light yellow crystals were obtained in an amount of 94.5 g at an yield of 107.67.

As a result of a gas-chromotographic analysis, it was confirmed that the molar ratio of 7-bromo-isomer to 6-bromo-isomer was 3.8:1.

Examples 1 to 9 clearly show that 7-bromo-β-carboline compounds of the formula (I) can be produced at a high yield and a high selectivity by the method of the present invention.

The 7-bromo-β-carboline compounds of the formula (I) can be converted into various alkaloid compounds useful as a medicine or as a precursory of a medicine.

REFERENTIAL EXAMPLE 1

Preparation of 16-bromovincadifformine

A dispersion of 38.8 g (0.12 mole) of 7-bromo-1-methyl-1-methoxycarbonyl-1,2,3,4-tetrahydro-β-carboline and 13.8 g (0.14 mole) of sodium propionate in 600 ml of cyclohexane was mixed with 278.8 g (0.14 mole) of 5-bromo-2-ethylpentanal and 3.2 g of propionic acid. The reaction mixture was heated under reflux for 48 hours while distilling away an azeotropic mixture of the solvent (cyclohexane) with water which was produced as a reaction by-product. The resultant reaction mixture was cooled and any non-dissolved substance removed therefrom by filtration. The filtration was washed with 100 ml of a 10% sodium carbonate aqueous solution and then twice with 100 ml of water, and the washed filtrate was distilled under a reduced pressure to remove the solvent. The resultant distillation residue in the form of a red oily liquid was dissolved in 65 ml of isopropyl alcohol at an elevated temperature, and the resultant solution was admixed with 12 g of oxalic acid dihydrate.

The resultant deposit was separated by filtration.

16-bromovincadifformine oxalic acid salt in the form of a white powder was obtained in an amount of 34.0 g at a yield of 56%.

REFERENTIAL EXAMPLE 2

Preparation of 11-bromovincamine

The 16-bromovincadifformine oxalic acid salt in an amount of 12.2 g was dissolved in a mixture solvent consisting of water and methyl alcohol in a mixing weight ratio of 1:1. The resultant solution was mixed with 50 ml of toluene and an aqueous solution of potassium carbonate was added dropwise to the mixture until the resultant water phase was sufficiently alkaline. The resultant toluene phase was separated from the water phase, washed with water, and then distilled under a reduced pressure to remove toluene. The crystalline residue was dissolved in 50 ml of methyl alcohol, and was mixed with 0.2 g of tungstic acid. Then, 14 g of a 30% hydrogen peroxide aqueous solution was added dropwise to the solution. The mixture was heated under reflux for 8 hours while stirring the mixture. The mixture was cooled to room temperature, and extracted with dichloromethane. The dichloromethane phase was separated from the mixture and was distilled under a reduced pressure to remove dichloromethane. The residual viscous substance was dissolved in methyl alcohol at an elevated temperature. The solution was mixed with a Raney nickel catalyst and the mixture was stirred at room temperature under a hydrogen gas pressure of 5 kg/cm$^2$ for 8 hours. The catalyst was removed from the mixture by filtration. The residual solution was mixed with a concentrated hydrochloric acid to adjust the pH of the solution to 2.5 and the solution was further stirred at a temperature of 50° C. for 4 hours. Then, the solution was mixed with methyl alcohol and water in the same amount as the methylalcohol, and with a 10% sodium carbonate aqueous solution, in a dropwise manner to make the resultant solution alkaline. The resultant deposit was collected by filtration, and the collected solid substance was dispersed in and washed with acetonitril. The washed solid substance was collected again by filtration. The resultant light yellow powder was a mixture of 11-bromovincamine and epimer thereof in a weight ratio of 2:8, and was obtained at a yield of 56%.

The epimer-containing 11-bromovincamine mixture was dispersed in methyl alcohol in an amount of 4 times the amount of the mixture, and was admixed with 2% of a 28% NaOCH$_3$-methyl alcohol solution. The resultant admixture was heated with reflux for 6 hours, and was cooled with ice water, and the cooled admixture was then filtered to collect the resultant 11-bromovincamine in the form of white needle-shaped crystals at a yield of 90%.

We claim:

1. A method for producing a 7-bromo-$\beta$-carboline compound comprising the steps of:

(A) reacting a $\beta$-carboline compound of the formula (II):

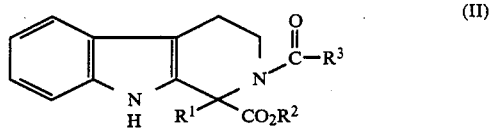

wherein R$^1$ represents a member selected from the group consisting of a hydrogen atom and alkyl radicals having 1 to 5 carbon atoms, R$^2$ represents a member selected from the group consisting of alkyl radicals having 1 to 5 carbon atoms and a benzyl radical, and R$^3$ represents a member selected from the group consisting of a hydrogen atom, alkyl radicals having 1 to 5 carbon atoms, alkoxy radicals having 1 to 5 carbon atoms and a benzyloxy radical, with a brominating agent selected from the group consisting of bromine and N-bromosuccinimide, in an amount of 0.8 to 1.5 molar equivalent weight per molar equivalent weight of the $\beta$-carboline compound of the formula (II), in an organic solvent in the presence of an alkali at a temperature lower than the boiling point of the organic solvent, to prepare a precursory 7-bromo-$\beta$-carboline compound of the formula (III):

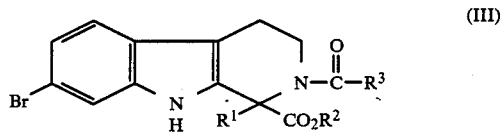

wherein R$^1$, R$^2$ and R$^3$ are as defined above; and (B) hydrolyzing the precursory compound of the formula (III) in a solvent in the presence of a mineral acid at a temperature of 80° C. or less, to provide a 7-bromo-$\beta$-carboline compound of the formula (I):

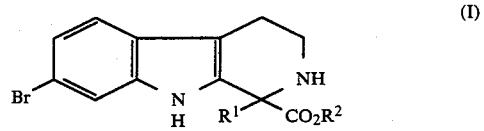

wherein R$^1$ and R$^2$ are as defined above.

2. The method as claimed in claim 1, wherein the compound of the formula (II) is selected from the group consisting of 2-formyl, 2-acetyl, 2-benzyloxycarbonyl and 2-tert-butyloxycarbonyl derivatives of 1-methoxycarbonyl-1,2,3,4-tetrahydro-$\beta$-carboline, 1-methyl-1-methoxycarbonyl-1,2,3,4-tetrahydro-$\beta$-carboline, 1-methyl-1-ethoxycarbonyl-1,2,3,4-tetrahydro-$\beta$-carboline and 1-ethyl-1-methoxycarbonyl-1,2,3,4-tetrahydro-$\beta$-carboline.

3. The method as claimed in claim 1, wherein the solvent is a member selected from the group consisting of chlorine-containing organic liquid compounds and polar organic liquid compounds.

4. The method as claimed in claim 1, wherein the alkali is a member selected from sodium hydrogen carbonate, potassium hydrogen carbonate, sodium carbonate, sodium hydrogen sulfate, and alkali metal salts of formic acid, acetic acid, propionic acid and benzoic acid.

5. The method as claimed in claim 1, wherein the alkali is used in an amount of 0.5 to 2.0 molar equivalent weight per molar equivalent weight of bromine.

6. The process as claimed in claim 1, wherein in step (B), the solvent is a member selected from the group consisting of alcohols, acetic acid and propionic acid.

7. The method as claimed in claim 1, wherein the mineral acid is a member seleted from the group consisting of hydrogen chloride and hydrogen bromide.

8. The method as claimed in claim 1, wherein the mineral acid is used in an amount of 1.0 to 3.0 molar equivalent weight per molar equivalent weight of the precursory 7-bromo-$\beta$-carboline compound of the formula (III).

9. The method as claimed in claim 1, wherein the 7-bromo-$\beta$-carboline compound of the formula (I) is selected from the group consisting of 7-bromo-1-methyl-1-methoxycarbonyl-1,2,3,4-tetrahydro-$\beta$-carboline-7-bromo-1-methyl-1-ethoxycarbonyl-1,2,3,4-tetrahydro-$\beta$-carboline, 7-bromo-1-ethoxycarbonyl-1,2,3,4-tetrahydro-$\beta$-carboline and 7-bromo-1-benzyloxycarbonyl-1,2,3,4-tetrahydro-$\beta$-carboline.

* * * * *